(12) United States Patent
Bouhnik et al.

(10) Patent No.: US 9,895,113 B2
(45) Date of Patent: Feb. 20, 2018

(54) SYSTEMS AND METHODS FOR PLANAR IMAGING WITH DETECTORS HAVING MOVING DETECTOR HEADS

(71) Applicant: General Electric Company, Schenectady, NY (US)

(72) Inventors: Jean-Paul Bouhnik, Tirat Carmel (IL); Yaron Hefetz, Kibbutz Alonim (IL)

(73) Assignee: General Electric Company, Schenectady, NY (US)

( * ) Notice: Subject to any disclaimer, the term of this patent is extended or adjusted under 35 U.S.C. 154(b) by 564 days.

(21) Appl. No.: 14/040,079

(22) Filed: Sep. 27, 2013

(65) Prior Publication Data
US 2015/0094573 A1 Apr. 2, 2015

(51) Int. Cl.
*A61B 6/03* (2006.01)
*A61B 6/00* (2006.01)
*G01T 1/29* (2006.01)

(52) U.S. Cl.
CPC ............ *A61B 6/037* (2013.01); *A61B 6/4258* (2013.01); *A61B 6/4266* (2013.01); *A61B 6/4275* (2013.01); *G01T 1/2985* (2013.01); *A61B 6/4233* (2013.01)

(58) Field of Classification Search
None
See application file for complete search history.

(56) References Cited

U.S. PATENT DOCUMENTS

| | | | | |
|---|---|---|---|---|
| 2004/0262525 A1* | 12/2004 | Yunker | ................. | G01T 1/1648 250/363.08 |
| 2006/0081899 A1* | 4/2006 | Fritzler | ................. | G01T 1/1614 257/291 |
| 2010/0193696 A1* | 8/2010 | Blevis | .................... | G01T 1/249 250/370.08 |
| 2011/0026685 A1* | 2/2011 | Zilberstein | ........... | G01T 1/1611 378/197 |
| 2012/0236985 A1* | 9/2012 | Schusser | ................. | G21K 1/06 378/16 |

* cited by examiner

*Primary Examiner* — Katherine Fernandez
*Assistant Examiner* — Marjan Saboktakin
(74) *Attorney, Agent, or Firm* — Dean D. Small; The Small Patent Law Group, LLC

(57) ABSTRACT

Systems and methods for planar imaging with detectors having moving heads are provided. One system includes a gantry having an opening therethrough, a patient table movable through the opening of the gantry along an examination axis, and a plurality of detector units mounted to the gantry and aligned in a row transverse to the examination axis. The plurality of detector units are spaced apart from each other, wherein the spacing forms gaps between adjacent detector units. The plurality of detector units are configured to acquire Single Photon Emission Computed Tomography (SPECT) data. The system further includes a controller configured to control movement of the patient table and the plurality of detector units to acquire two-dimensional (2D) SPECT data, wherein the plurality of detector units remain in a fixed relative orientation with respect to each other when acquiring the 2D SPECT data and move together to acquire the 2D SPECT data.

11 Claims, 15 Drawing Sheets

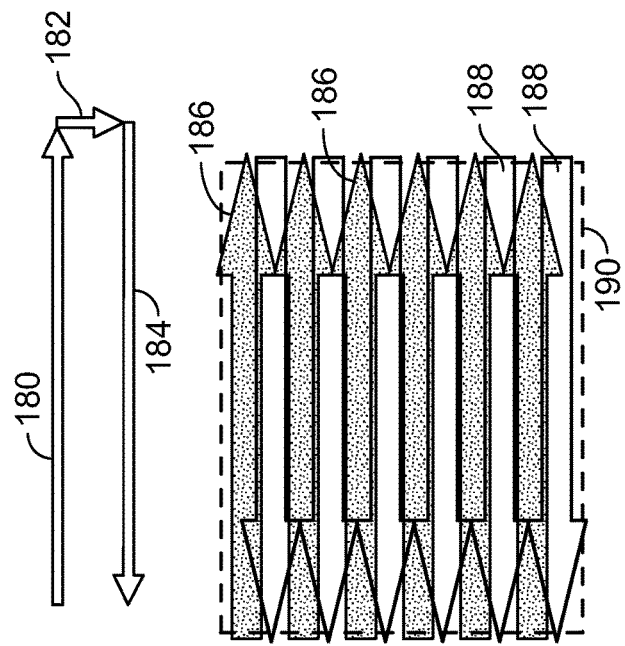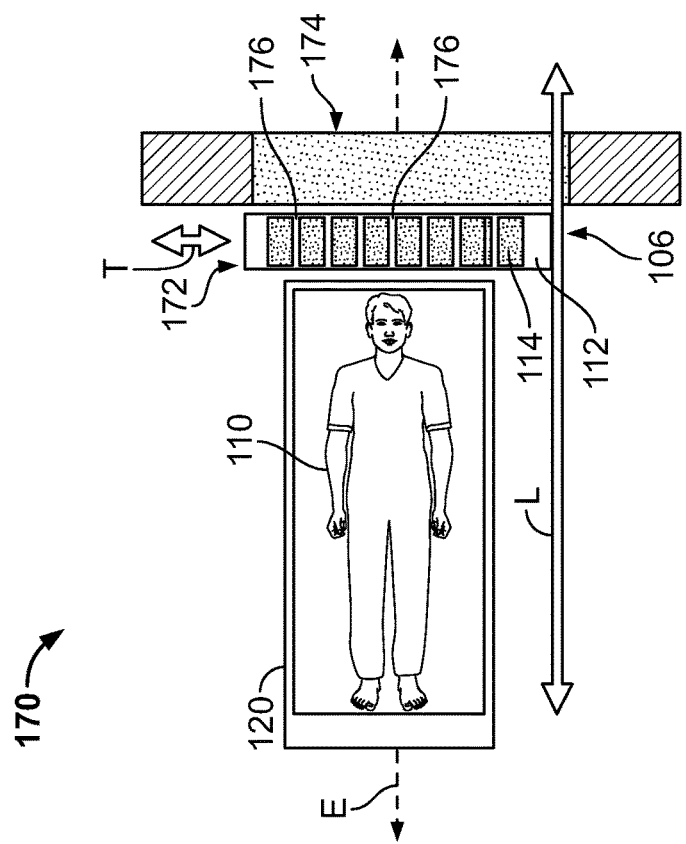

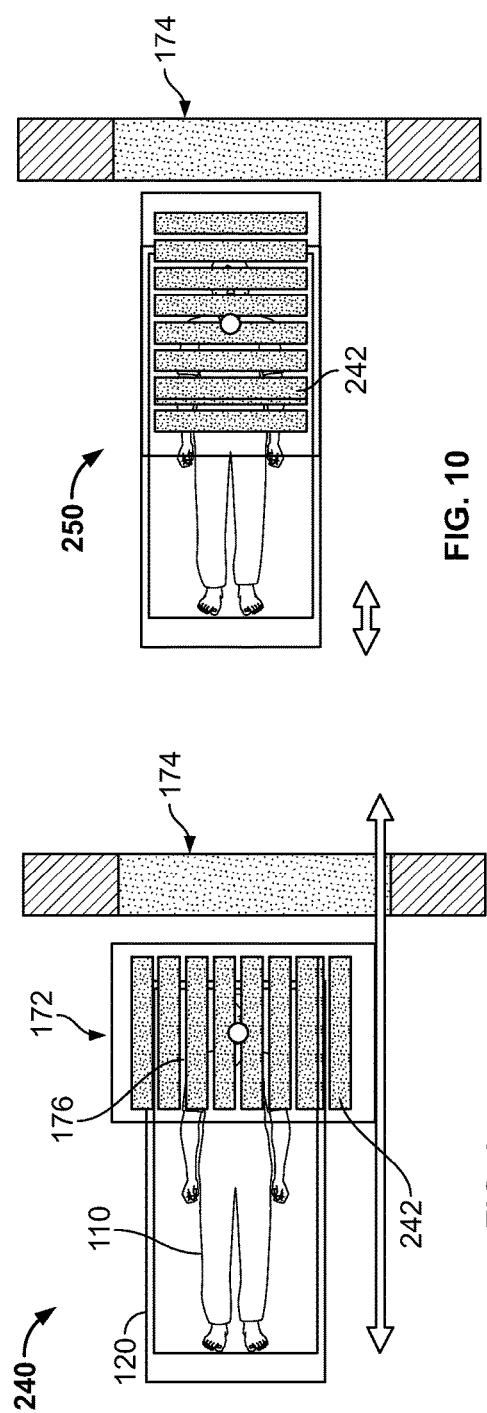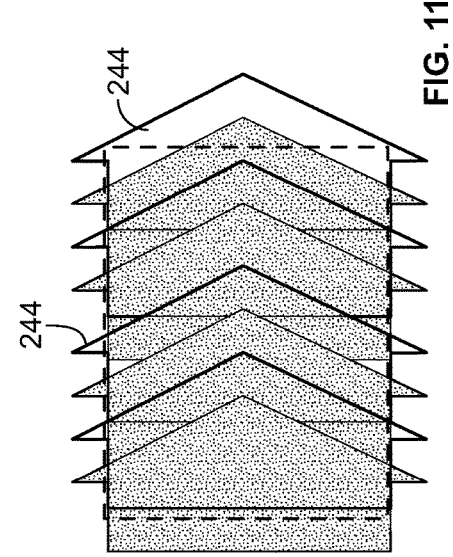

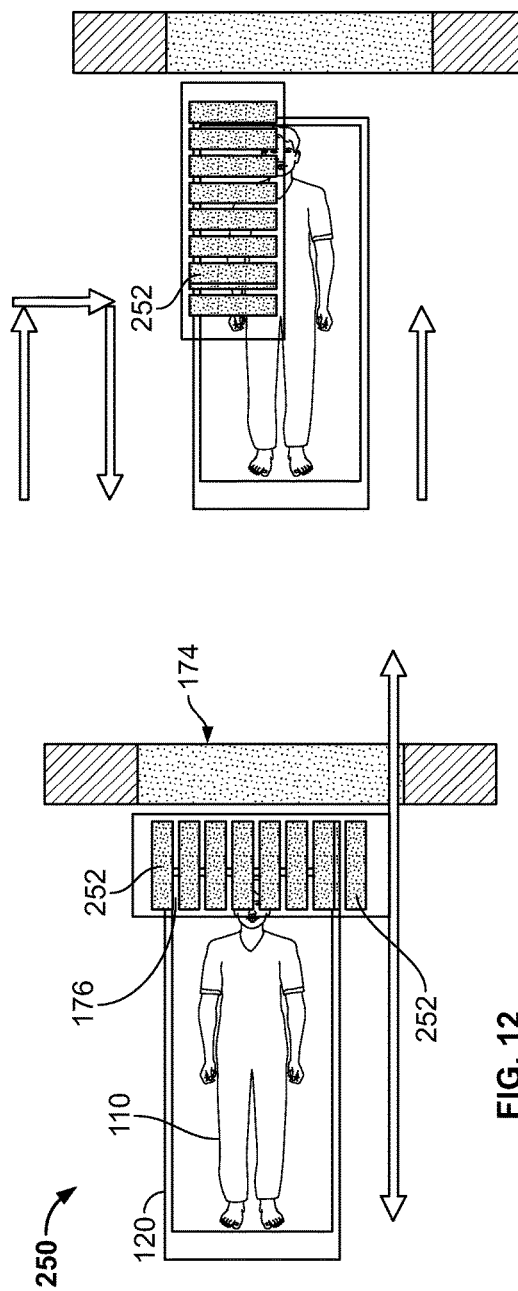
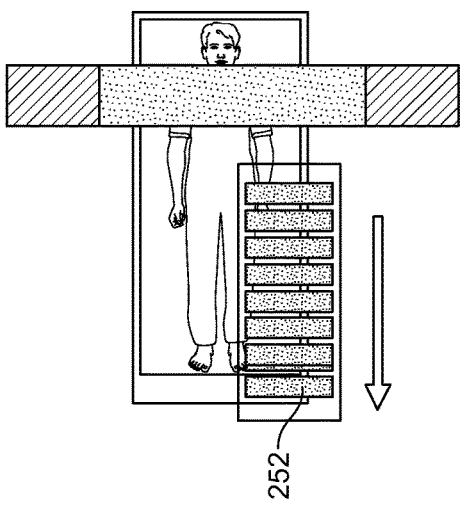
FIG. 12
FIG. 13
FIG. 14

SYSTEMS AND METHODS FOR PLANAR IMAGING WITH DETECTORS HAVING MOVING DETECTOR HEADS

BACKGROUND OF THE INVENTION

The subject matter disclosed herein relates generally to apparatus and methods for diagnostic medical imaging, such as Nuclear Medicine (NM) imaging.

In NM imaging, systems with multiple detectors or detector heads may be used to image a subject, such as to scan a region of interest. For example, the detectors may be positioned adjacent the subject to acquire NM data, which is used to generate a three-dimensional (3D) image of the subject.

Single Photon Emission Computed Tomography (SPECT) systems may have moving detector heads positioned to focus on a region of interest. For example, a number of pinhole gamma cameras may be moved (e.g., rotated or swung) to different angular positions for acquiring image data. The acquired image data is then used to generate the 3D images. However, in these SPECT systems, two-dimensional (2D) image acquisition is not provided. Accordingly, if a 2D image is desired, one or more of the 3D images are converted to a 2D image. Thus, even when only 2D images are desired, 3D image data is acquired in order to thereafter convert that data to 2D images. This process adds time to the overall scan and image reconstruction process.

BRIEF DESCRIPTION OF THE INVENTION

In one embodiment, an imaging system is provided that includes a gantry having an opening therethrough, a patient table movable through the opening of the gantry along an examination axis, and a plurality of detector units mounted to the gantry and aligned in a row transverse to the examination axis. The plurality of detector units are spaced apart from each other, wherein the spacing forms gaps between adjacent detector units. The plurality of detector units are configured to acquire Single Photon Emission Computed Tomography (SPECT) data. The imaging system further includes a controller configured to control movement of the patient table and the plurality of detector units to acquire two-dimensional (2D) SPECT data, wherein the plurality of detector units remain in a fixed relative orientation with respect to each other when acquiring the 2D SPECT data and move together to acquire the 2D SPECT data.

In another embodiment, an imaging system is provided that includes a gantry having an opening therethrough, a patient table movable through the opening of the gantry along an examination axis, and a plurality of detector units mounted to the gantry and aligned in a row. The plurality of detector units are movable to acquire Single Photon Emission Computed Tomography (SPECT) data. The imaging system further includes a controller configured to control movement of the patient table and the plurality of detector units (i) as a group to acquire two-dimensional (2D) SPECT data, the plurality of detector units remaining in a fixed relative orientation with respect to each other when acquiring the 2D SPECT data, and (ii) individually to acquire three-dimensional (3D) SPECT data, the plurality of detector units individually moving with respect to each other when acquiring the 3D SPECT data.

In another embodiment, a method to acquire two-dimensional (2D) Single Photon Emission Computed Tomography (SPECT) data is provided. The method includes aligning a patient table with an opening of a gantry and along an examination axis, wherein the patient table is movable through the opening of the gantry along the examination axis. A plurality of detector units is mounted to the gantry and aligned in a row, wherein the plurality of detector units are spaced apart from each other. The spacing forms gaps between adjacent detector units, wherein the plurality of detector units are configured to acquire Single Photon Emission Computed Tomography (SPECT) data. The method also includes controlling movement of the patient table and the plurality of detector units to acquire two-dimensional (2D) SPECT data, wherein the plurality of detector units remain in a fixed relative orientation with respect to each other when acquiring the 2D SPECT data and the plurality detector units move together to acquire the 2D SPECT data.

BRIEF DESCRIPTION OF THE DRAWINGS

FIG. 2 is a diagram of an imaging system having a detector configuration in accordance with an embodiment.

FIG. 3 is a diagram illustrating data acquisition scan movement in accordance with an embodiment.

FIGS. 9 and 10 are diagrams of imaging systems having a detector configuration in accordance with another embodiment.

FIG. 11 is a diagram illustrating data acquisition scan movement in accordance with another embodiment.

FIGS. 12-14 are diagrams of an imaging system having a detector configuration in accordance with another embodiment.

DETAILED DESCRIPTION OF THE INVENTION

Figure 1:
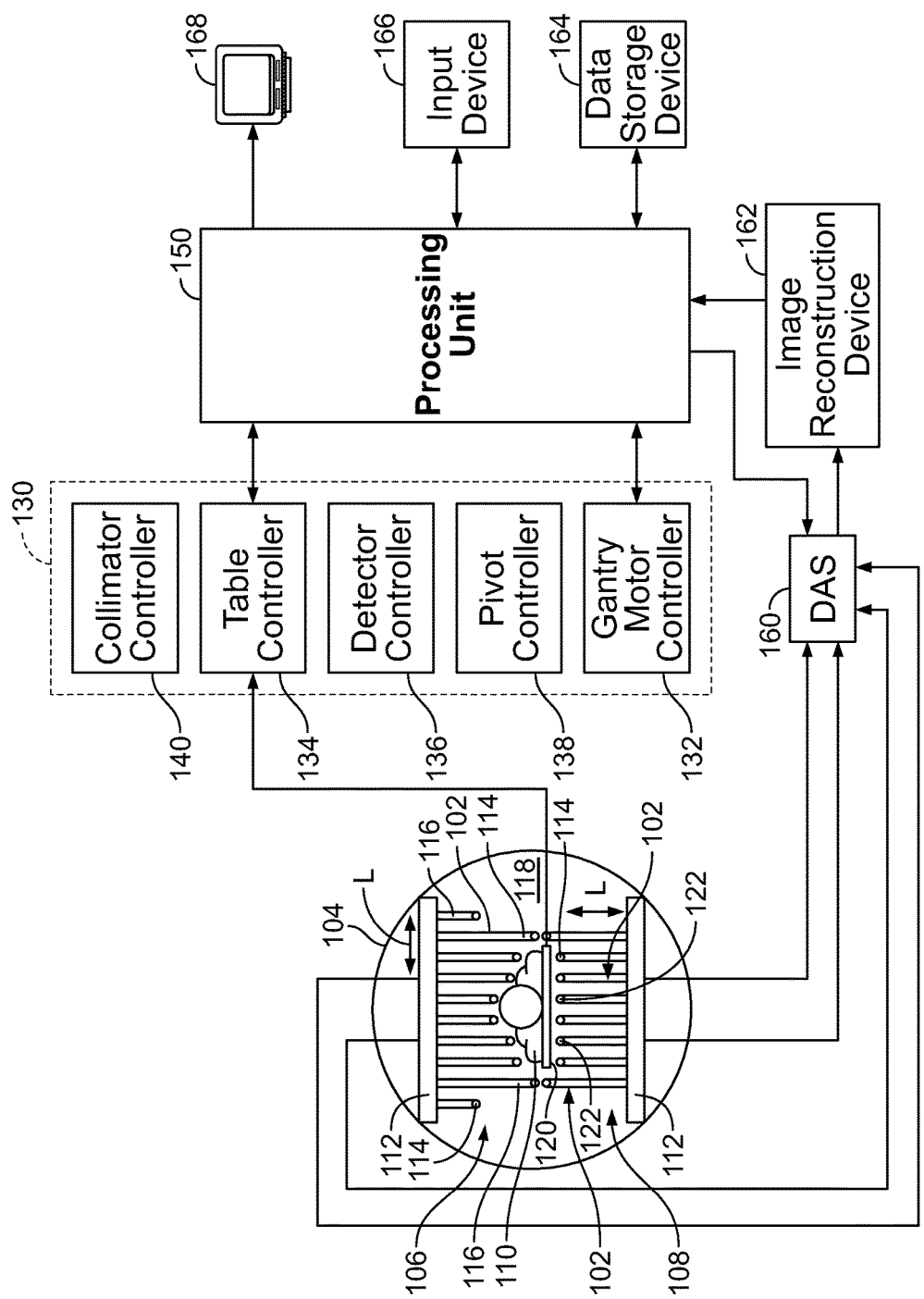
FIG. 1 is a schematic block diagram of a Nuclear Medicine (NM) imaging system in accordance with an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for controlling the movement of a plurality of imaging detectors to position the imaging detectors to acquire two-dimensional (2D) planar images. For example, in various embodiments, an imaging system having one or more Nuclear Medicine (NM) cameras having an array of heads that are individually and independently movable is provided. In some embodiments, one or more of the heads are capable of a plurality of types of movement, such as rotation and parallel linear motion. For example, the detector heads may be configured to swing, pivot, or rotate. The NM camera is configured to acquire Single Photon Emission Computed Tomography (SPECT), such as when moving the detector heads. Accordingly, in this mode of operation with the detector heads moving, the system acquires 3D image data. In other embodiments, as described in more detail herein, the NM cameras are controlled to acquire 2D image data and generate 2D images directly from the acquired data. For example, the NM cameras are controlled in a mode where the detector heads are not moving and acquire 2D image data. Thus, in various embodiments, the movement of the detector heads is controlled to account for gaps therebetween while acquiring 2D images (also referred to as planar images), wherein the gaps are provided to allow for rotation of the detector heads in some modes of operation, such as to acquire 3D images.

At least one technical effect of some embodiments is acquiring 2D NM data using a SPECT imaging system having a plurality of moving detector heads. For example, in various embodiments, the detector heads are arranged in an array and configured for rotatable movement.

FIG. 1 is a schematic illustration of a NM imaging system 100 having a plurality of imaging detectors mounted on a gantry. In particular, a plurality of imaging detectors 102 are mounted to a gantry 104. In the illustrated embodiment, the imaging detectors 102 are configured as two separate detector arrays 106 and 108 coupled to the gantry 104 above and below a subject 110 (e.g., a patient), as viewed in FIG. 1. The detector arrays 106 and 108 may be coupled directly to the gantry 104, or may be coupled via support members 112 to the gantry 104 to allow movement of the entire arrays 106 and/or 108 relative to the gantry 104 (e.g., translating movement in the left or right direction as viewed in FIG. 1). Additionally, each of the imaging detectors 102 includes a detector unit 114, at least some of which are mounted to a movable detector carrier 116 (e.g., a support arm or actuator that may be driven by a motor to cause movement thereof) that extends from the gantry 104. In some embodiments, the detector carriers 116 allow movement of the detector units 114 towards and away from the subject 110, such as linearly. Thus, in the illustrated embodiment the detector arrays 106 and 108 are mounted in parallel above and below the subject 110 and allow linear movement of the detector units 114 in one direction (indicated by the arrow L), illustrated as perpendicular to the support member 112 (that are coupled generally horizontally on the gantry 104). However, other configurations and orientations are possible as described herein. It should be noted that the movable detector carrier 116 may be any type of support that allows movement of the detector units 114 relative to the support member 112 and/or gantry 104, which in various embodiments allows the detector units 114 to move linearly towards and away from the support member 112.

Each of the imaging detectors 102 in various embodiments are smaller than a conventional whole body or general purpose imaging detector. A conventional imaging detector may be large enough to image most or all of a width of a patient's body at one time and may have a diameter of approximately 50 cm or more. In contrast, each of the imaging detectors 102 may include one or more detector units 114 coupled to a respective detector carrier 116 and having dimensions of 4 cm to 20 cm and may be formed of Cadmium Zinc Telluride (CZT) tiles or modules. For example, each of the detector units 114 may be 8×8 cm in size and be composed of a plurality of CZT pixelated modules (not shown). For example, each module may be 4×4 cm in size and have 16×16=256 pixels. In some embodiments, each detector unit 114 includes a plurality of modules, such as an array of 1×7 modules. However, different configurations and array sizes are contemplated including, for example, detector units 114 having multiple rows of modules.

It should be understood that the imaging detectors 102 may be different sizes and/or shapes with respect to each other, such as square, rectangular, circular or other shape. An actual field of view (FOV) of each of the imaging detectors 102 may be directly proportional to the size and shape of the respective imaging detector.

The gantry 110 may be formed with an aperture 118 (e.g., opening or bore) therethrough as illustrated. A patient table 120, such as a patient bed, is configured with a support mechanism (not shown) to support and carry the subject 110 in one or more of a plurality of viewing positions within the aperture 118 and relative to the imaging detectors 102. Alternatively, the gantry 104 may comprise a plurality of gantry segments (not shown), each of which may independently move a support member 112 or one or more of the imaging detectors 102.

The gantry 104 may also be configured in other shapes, such as a "C", "H" and "L", for example, and may be rotatable about the subject 110. For example, the gantry 104 may be formed as a closed ring or circle, or as an open arc or arch which allows the subject 110 to be easily accessed while imaging and facilitates loading and unloading of the subject 110, as well as reducing claustrophobia in some subjects 110.

Additional imaging detectors (not shown) may be positioned to form rows of detector arrays or an arc or ring around the subject 110. By positioning multiple imaging detectors 102 at multiple positions with respect to the subject 110, such as along an imaging axis (e.g., head to toe direction of the subject 110) image data specific for a larger FOV may be acquired more quickly.

Each of the imaging detectors 102 has a radiation detection face, which is directed towards the subject 110 or a region of interest within the subject. The radiation detection faces are each covered by or have coupled thereto a collimator 122. The actual FOV for each of the imaging detectors 102 may be increased, decreased, or relatively unchanged by the type of collimator 122. In one embodiment, the collimator 122 is a multi-bore collimator, such as a parallel hole collimator. However, other types of collimators, such as converging or diverging collimators may optionally or alternatively be used. Other examples for the collimator 122 include pinhole, parallel-beam converging, diverging fan-beam, converging or diverging cone-beam, multi-bore converging, multi-bore converging fan-beam, multi-bore converging cone-beam, multi-bore diverging, or other types of collimator.

Optionally, multi-bore collimators may be constructed to be registered with pixels of the detector units 114, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or inbetween two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 130 may control the movement and positioning of the patient table 110, imaging detectors 102, gantry 104 and/or the collimators 122. A range of motion before or during an acquisition, or between different image acquisitions, is set to maintain the actual FOV of each of the imaging detectors 102 directed, for example, towards or "aimed at" a particular area or region of the subject 110 or along the entire subject 110.

The controller unit 130 may have a gantry motor controller 132, table controller 134, detector controller 136, pivot controller 138, and collimator controller 140. The controllers 130, 132, 134, 136, 138, 140 may be automatically commanded by a processing unit 150, manually controlled by an operator, or a combination thereof. The gantry motor controller 132 may move the imaging detectors 102 with respect to the subject 110, for example, individually, in segments or subsets, or simultaneously in a fixed relationship to one another. For example, in some embodiments, the gantry controller 132 may cause the imaging detectors 102 and/or support members 112 to move relative to or rotate about the subject 110, which may include motion of less than or up to 180 degrees (or more).

The table controller 134 may move the patient table 120 to position the subject 110 relative to the imaging detectors 102. The patient table 120 may be moved in up-down directions, in-out directions, and right-left directions, for example. The detector controller 136 may control movement of each of the imaging detectors 102 to move together as a group or individually as described in more detail herein. The detector controller 136 also may control movement of the imaging detectors 102 in some embodiments to move closer to and farther from a surface of the subject 110, such as by controlling translating movement of the detector carriers 116 linearly towards or away from the subject 110 (e.g., sliding or telescoping movement). Optionally, the detector controller 136 may control movement of the detector carriers 116 to allow movement of the detector array 106 or 108. For example, the detector controller 136 may control lateral movement of the detector carriers 116 illustrated by the L arrow (and shown as left and right as viewed in FIG. 1). In various embodiments, the detector controller 136 may control the detector carriers 116 or the support members 112 to move in different lateral directions or patterns to acquire 2D image data as described in more detail herein. For example, in some embodiments, a 2D imaging mode is provided wherein the detector units 114 are not individually moved (e.g., rotated) for image acquisition, but instead the entire detector array 106 and/or 108 is moved to perform 2D NM imaging. It should be noted that various embodiments also may be implemented in SPECT systems wherein the individual detectors, such as the detector units 114, are not capable of movement or motion (e.g., individual and independent rotating movement).

The pivot controller 138 may control pivoting movement of the detector units 114 at ends of the detector carriers 116 and/or pivoting movement of the detector carrier 116. For example, one or more of the detector units 114 or detector carriers 116 may be rotated about at least one axis to view the subject 110 from a plurality of angular orientations to acquire, for example, 3D image data in a 3D SPECT or 3D imaging mode of operation. The collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and optionally, motions in several motion directions may be used. Therefore, the term "motion controller" may be used to indicate a collective name for all motion controllers. It should be noted that the various controllers may be combined, for example, the detector controller 136 and pivot controller 138 may be combined to provide the different movements described herein.

Prior to acquiring an image of the subject 110 or a portion of the subject 110, the imaging detectors 110, gantry 104, patient table 120 and/or collimators 122 may be adjusted as discussed in more detail herein, such as to first or initial imaging positions, as well as subsequent imaging positions. The imaging detectors 102 may each be positioned to image a portion of the subject 110. Alternatively, one or more of the imaging detectors 102 may not be used to acquire data, such as the imaging detectors 102 at ends of the detector arrays 106 and 108, which as illustrated in FIG. 1 are in a retracted position away from the subject 110. Positioning may be accomplished manually by the operator and/or automatically, which may include using other images acquired before the current acquisition, such as by another imaging modality such as CT, MRI, X-Ray, PET or ultrasound. Additionally, the detector units 114 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 102, gantry 104, patient table 120, and/or collimators 122 are positioned, one or more 2D images are acquired using one or more of the imaging detectors 102. The image data acquired by each imaging detector 102 may be combined and reconstructed into a composite image or 2D images in various embodiments.

In one embodiment, at least one of detector arrays 106 and/or 108, gantry 104, patient table 120, and/or collimators 122 are moved after being initially positioned, which does not include any individual movement of the detector units 114 (e.g., pivoting movement). For example, at least one of detector arrays 106 and/or 108 may be moved laterally and in a parallel plane to the subject 110. Thus, in various embodiments, a plurality of small sized detectors, such as the detector units 114 that may be used for 3D imaging (such as when moving or sweeping), are controlled to perform 2D or planar imaging.

In various embodiments, a data acquisition system (DAS) 160 receives electrical signal data produced by the imaging detectors 102 and converts this data into digital signals for subsequent processing. However, in other embodiments, digital signals are provided from the detector units 114. An image reconstruction device 162 (which may be, for example, a processing machine or computer) and a data storage device 164 may be provided in addition to the processing unit 150. It should be noted that one or more functions related to one or more of data acquisition, motion control, data processing and image reconstruction may be accomplished through hardware, software and/or by shared processing resources, which may be located within or near the imaging system 100, or may be located remotely. Additionally, a user input device 166 may be provided to receive user inputs (e.g., control commands), as well as a display 168 for displaying images.

In operation, and as shown, for example, in FIG. 2, the motion of the detector array 106 and/or 108 (only the detector array 106 is shown in the top view of FIG. 2) is moved to acquired 2D images of the subject 110 supported on the patient table 120. In the illustrated embodiment, an imaging system 170 is provided that is a multi-modality imaging system having a NM imaging gantry 172 and an x-ray CT imaging gantry 174 that may be positioned in adjacent alignment defining a common and/or aligned bore therethrough along an examination axis (E). It should be noted that the NM image gantry 172 may be embodied as or form part of the NM imaging system 100 (shown in FIG. 1). The configuration and operation of the imaging system 170 to use image data from both modalities may be performed in different manners as described herein or as known in the art.

As can be seen, a gap 176 exists between adjacent detector units 114. For example, the gap 176 is provided in various embodiments to allow a range of individual and/or independent pivoting, rotation, or swiveling of the detector units 114. In the illustrated embodiment, the detector units 114 are maintained in a non-rotated state such that a detecting surface of each of the detector units 114 is parallel to the patient table 110. It should be noted that the number of detector units 114 shown is merely for illustration and additional or fewer detector units 114 may be provided. In some embodiments, multiple rows of detector units 114 may be provided, such as in parallel alignment.

In the illustrated embodiment, the number of detector units 114 provided is selected such that coverage extends at least the width of the patient table 120 (shown as wider than the patient table 120). In operation in this embodiment, the patient table 120 is moved linearly along the examination axis as illustrated by the L arrow. For example, the patient table 120 is moved into and out of the common bore or aperture 118 (shown in FIG. 1) such that the subject 110 is moved through or past the detector units 114. Additionally, the detector units 114 are controlled to move together linearly and in a lateral motion transverse to the examination axis as illustrated by the T arrow. The motion in the direction of the T arrow in the illustrated embodiment is perpendicular to the examination axis and may be in either direction along the axis identified by the T arrow.

In operation in this embodiment, 2D or planar images are acquired by the motions illustrated in FIG. 3. In particular, with the detector units 114 positioned as shown, the patient table 120 is moved along the examination axis as indicated by the arrow 180 such that the subject 110 is moved into and through the field of view of the detector units 114. In one embodiment, the patient table 110 is moved such that the entire subject 110 moves past and is imaged by the detector units 114. The movement of the patient table 120 may be continuous or incremental (e.g., step wise).

Once the patient table 120 is moved such that the entire subject 110 is moved past the detector units 114, the detector units 114 are shifted as illustrated by the arrow 182. For example, the support member 112 in some embodiment is moved laterally to shift the detector units 114 in an axis perpendicular to the examination axis and along the T arrow as shown in FIG. 2. In one embodiment, the shift of the detector units 114 may be in either direction relative to the subject 110 (i.e., to the left or to the right of the subject 110). For example, the detector units 114 may be shifted by half of the distance of the gap 176. However, other shift amounts are contemplated. For example, the detector units 114 may be shifted by the entire distance of the gap 176 or by a percentage of the width of the detector units 114, such as half the width of the detector units 114.

After the detector units 114 are shifted, the patient table 120 is again moved, which is illustrated by the arrow 184 (in an opposite direction to the arrow 180). For example, the patient table 120 may now be moved to move the entire subject 110 past the detector units 114, but the opposite direction along the examination axis. Thus, two scans or passes of the entire subject 110 are performed with the detector units 114 in different shifted positions for each of the scans or passes. Thus, full coverage of the imaging range is provided as illustrated by the arrows 186 and 188 showing the axes of movement of the detector units 114. For example, an entire imaging area 190 is covered using the motions illustrated by the arrows 180, 182, 184.

It should be noted that the detector units 114 are acquiring image data of the subject 110 as the subject 110 is moved along the examination axis past the detector units 114 in both directions. This acquired data is 2D data, which then may be used to reconstruct or generate 2D or planar images of the subject 110, such as using image reconstruction methods of the art. Thus, the motions illustrated by the arrows 180, 182, 184 define trajectories of motion that encompass the entire 2D plane of the subject 110.

Figure 4:
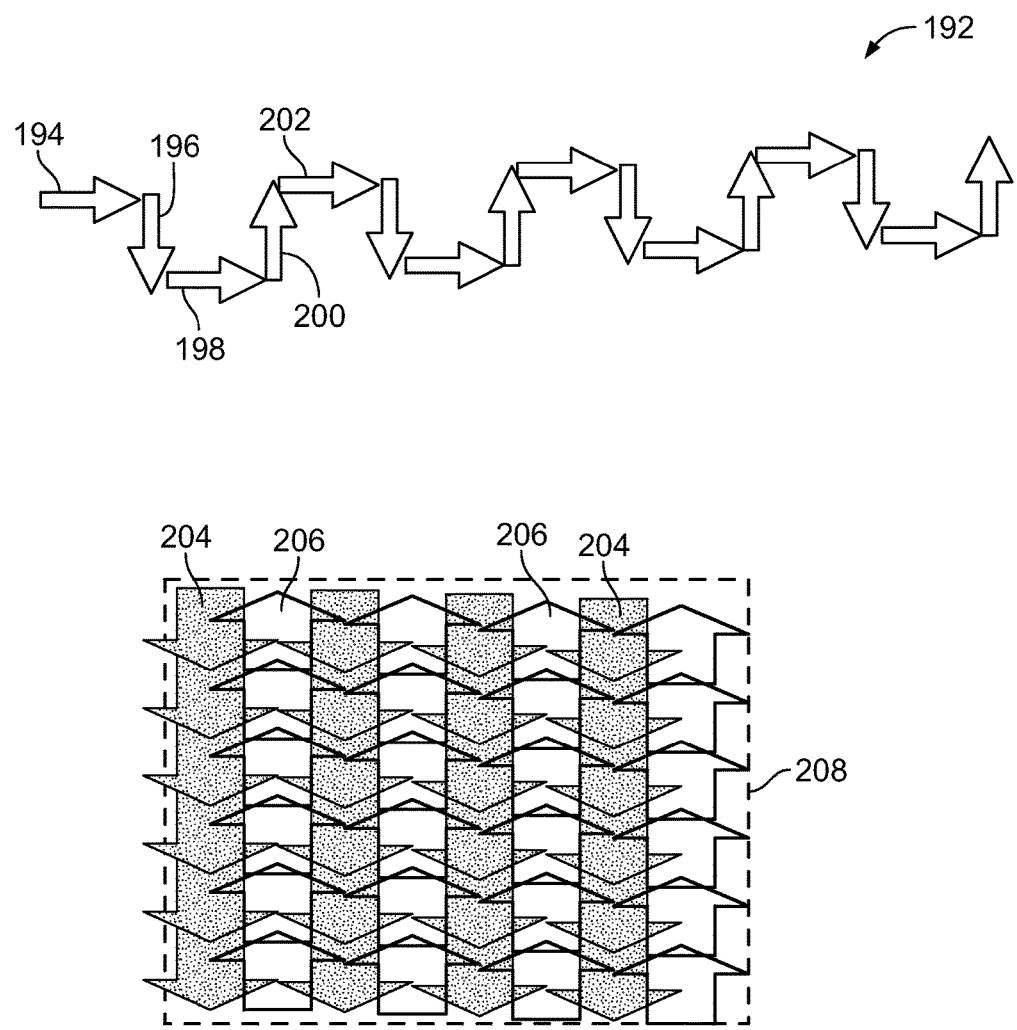
FIG. 4 is a diagram illustrating data acquisition scan movement in accordance with another embodiment.

Variations and modifications are contemplated. For example, the imaging system 170 may be moved as illustrated in FIG. 4 to acquire 2D or planar images. The illustrated motion in this embodiment is a zig-zag pattern 192 that provides full coverage of the subject 110. It should be noted that the different scanning patterns may be provided by moving or shifting of the patient table 120, the detector units 114, or a combination thereof. In this embodiment, the patient table 120 or detector arrays are controlled such that movement is along an axis indicated by the arrow 194, then shifted (illustrated as a 90 degree shift) as indicated by the arrow 196. It should be noted that while the lengths of the arrows 194 and 196 indicate in this embodiment that a same distance in traveled in each direction for each segment of the zig-zag pattern 192, different lengths of movement may be provided as desired or needed. As can be seen, thereafter another shift (illustrated as a 90 degree shift) as indicated by the arrow 198 is performed, which is a shift in the opposite direction to the previous shift. Accordingly, in the illustrated embodiment, the direction of travel represented by the arrows 194 and 198 is in the same direction, but along different parallel paths. Thus, for example, the detector units 114 may together be shifted to move along these different paths.

Thereafter, another shift (illustrated as a 90 degree shift) as indicated by the arrow 200 is performed, which is a shift in the opposite direction to the previous shift. In this case, the direction of travel is parallel to, but in the opposite direction to the direction of travel corresponding to the arrow 196. Then, another shift (illustrated as a 90 degree shift) as indicated by the arrow 202 is performed, which is a shift in the opposite direction to the previous shift and returns to the original path of travel, namely in the same direction and along the same axis as arrow 194. This pattern may be repeated a number of times (as illustrated by the repeating pattern of arrows) to provide a complete scan or complete coverage for scanning the subject 110.

It should be noted that in some embodiments, for example, the movement to cause the shifts to the directions indicated by the arrows 196 and 200 are performed by moving the support member 112 laterally to shift the detector units 114. Additionally, the movement along the direction of travel corresponding to the arrows 194, 198, and 202 may be accomplished by movement of the patient table 120.

Thus, full coverage of the imaging range is provided as illustrated by the arrows 204 and 206 showing the axes of movement of the detector units 114 and/or patient table 120. For example, an entire imaging area 208 is covered using the motions illustrated by the zig-zag pattern 192.

It should be noted that the detector units 114 are acquiring image data of the subject 110 as the subject 110 is moved along the examination axis past the detector units 114 in both directions. This acquired data is 2D data, which then may be used to reconstruct or generate 2D or planar images of the subject 110, such as using image reconstruction methods of the art. Thus, the motions illustrated by the arrows 180, 182, 184 define trajectories of motion that encompass the entire 2D plane of the subject 110.

Figure 6:
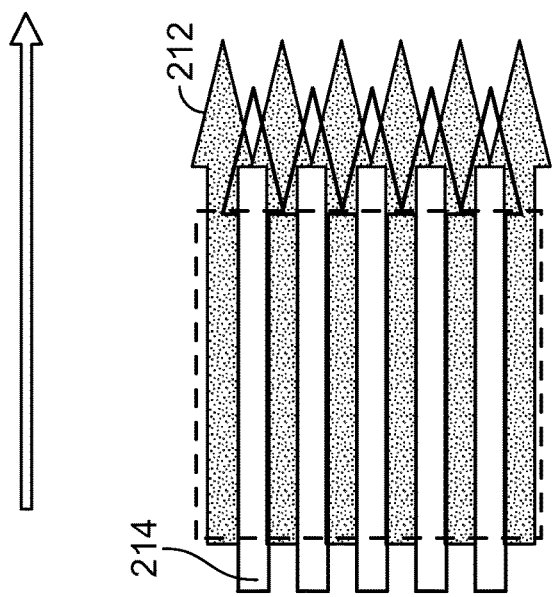
FIG. 6 is a diagram illustrating data acquisition scan movement in accordance with another embodiment.
Figure 5:
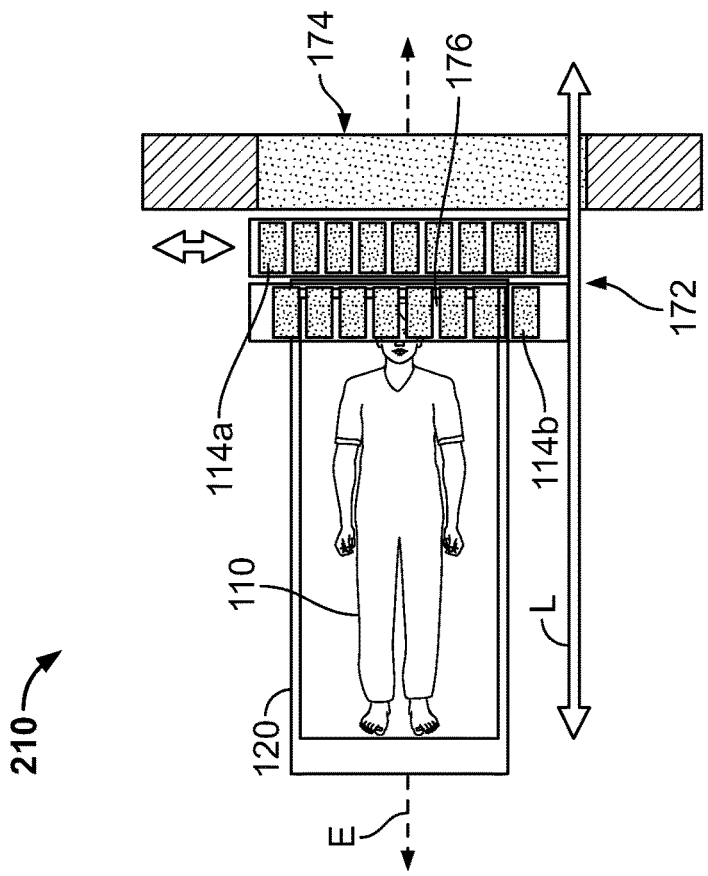
FIG. 5 is a diagram of an imaging system having a detector configuration in accordance with another embodiment.

Another detector configuration is shown in FIG. 5 and one embodiment of an operation thereof is shown in FIG. 6. In the illustrated embodiment, an imaging system 210 is provided that is a multi-modality imaging system having the NM imaging gantry 172 and the x-ray CT imaging gantry 174 that may be positioned in adjacent alignment defining a common and/or aligned bore therethrough along an examination axis (E). It should be noted that the NM image gantry 172 may be embodied as or form part of the NM imaging system 100 (shown in FIG. 1). The configuration and operation of the imaging system 170 to use image data from both modalities may be performed in different manners as described herein or as known in the art.

As can be seen, the gap 176 exists between adjacent detector units 114*a*, which defines a first detector row in the embodiment. For example, the gap 176 is provided in various embodiments to allow a range of individual and/or independent movement of the detector units 114. In the illustrated embodiment, the detector units 114 are maintained in a non-rotated state such that a detecting surface of each of the detector units 114 is parallel to the patient table 110. It should be noted that the number of detector units 114 shown is merely for illustration and additional or fewer detector units 114 may be provided. In this embodiment, however, different than FIG. 2, multiple rows of detector units 114 are provided, illustrated in parallel alignment. In this embodiment, two detector rows are shown, in particular the row of detector units 114*a* in parallel to the row of detector units 114*b*. It should be noted that the size and number of detector units 114*a* and 114*b* in each row may be the same or different.

In the illustrated embodiment, the number of detector units 114 provided is selected such that coverage extends at least the width of the patient table 120 (shown as wider than the patient table 120). As can be seen, the detector units 114*a* and 114*b* in different rows are offset to define staggered detector rows. For example, in the illustrated embodiment, the detector units 114*a* are offset or shifted laterally (in a direction perpendicular to the examination axis) with respect to the detector units 114*b*. Thus, the detector units 114*b* are aligned to extend at least across a corresponding gap 176 of the detector units 114*b*. For example, the gap 176 between detector units 114*a* or 114*b* align with at least a portion of a detector unit 114*b* or 114*a* in the adjacent row. Accordingly, the two row of detector units 114*a* and 114*b* provide complete coverage transverse to the examination axis (along the direction of travel of the patient table 120).

In operation in this embodiment, the patient table 120 is moved linearly along the examination axis as illustrated by the L arrow. For example, the patient table 120 is moved into and out of the common bore or aperture 118 (shown in FIG. 1) such that the subject 110 is moved through or past the detector units 114. However in this embodiment, the detector units 114 are not moved together linearly and in a lateral motion transverse to the examination axis (as performed in FIG. 2).

In operation in this embodiment, 2D or planar images are acquired by the motions illustrated in FIG. 6. In particular, with the detector units 114 positioned as shown, the patient table 120 is moved along the examination axis as indicated by the arrow 212 and 214 (corresponding to the movement relative to the detector units 114*a* and 114*b*) such that the subject 110 is moved into and through the field of view of the detector units 114. In one embodiment, the patient table 110 is moved such that the entire subject 110 moves past and is imaged by the detector units 114. The movement of the patient table 120 may be continuous or incremental (e.g., step wise).

Once the patient table 120 is moved such that the entire subject 110 is moved past the detector units 114 a complete scan had been performed. Thus, a single bed motion scan in performed in this embodiment. For example, only one scan or pass of the entire subject 110 is performed. The patient table 120 may be again moved in an opposite direction to remove the subject 110. For example, the patient table 120 may now be moved to move the entire subject 110 in the opposite direction along the examination axis.

The acquired data is 2D data then may be used to reconstruct or generate 2D or planar images of the subject 110, such as using image reconstruction methods of the art. Thus, a single pass of the subject 110 encompasses the entire 2D plane of the subject 110.

Figure 7:
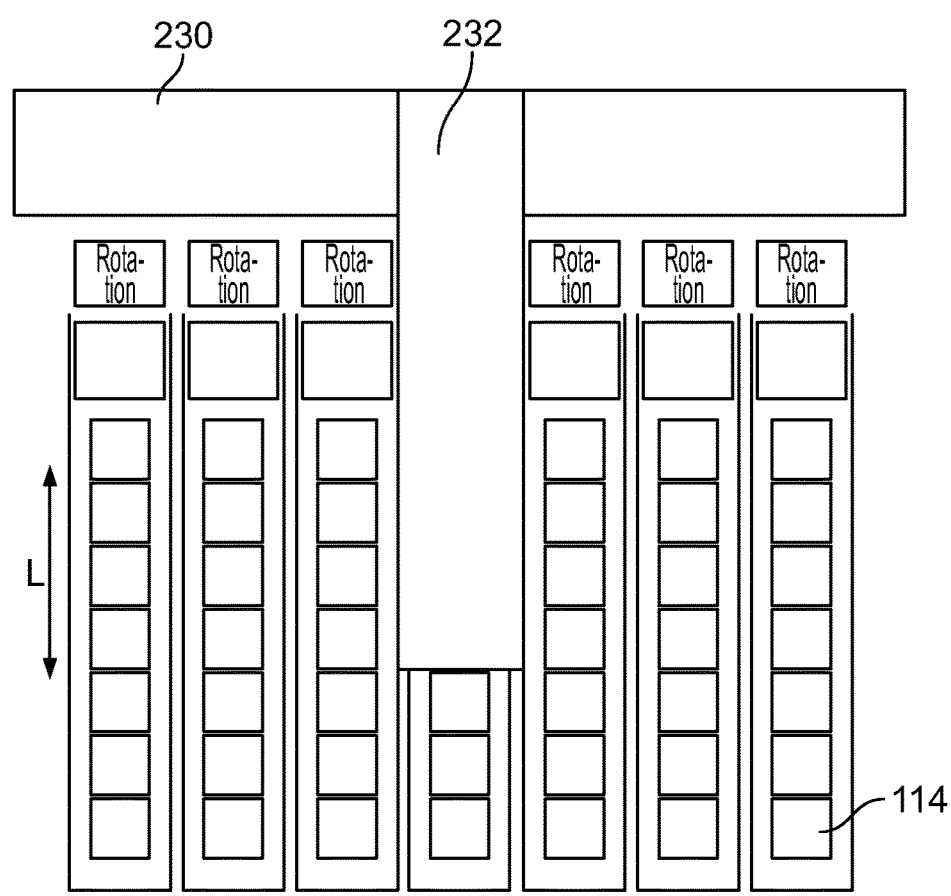
FIG. 7 is a diagram of a detector configuration in accordance with an embodiment.

In some embodiments, the detector units 114 are positioned differently when performing a 2D scan versus when a 3D scan is to be performed. For example, as illustrated in FIG. 7, a support structure 230 with an extending arm 232 coupled thereto may be provided. The arm 232 is coupled to a plurality of rows of detector units 114 (illustrated as seven rows, but more or less may be provided). It should be noted that any suitable mounting means may be used to mount the detector units 114 to the arm 232. For example, each row of detector units 114 may form a column that is coupled via a bracket (not shown) to the arm 232. In this 3D mode of operation the rows of detector units 114 are aligned along the examination axis (in the z direction) such that the length or longitudinal axis (L) is parallel with the examination axis. Additionally, in order to acquire 3D image data, the columns or rows of detector units 114 may oscillate, pivot, swivel, or rotate about an axis along L (e.g., rotate about a support rod within each of the columns).

Figure 8:
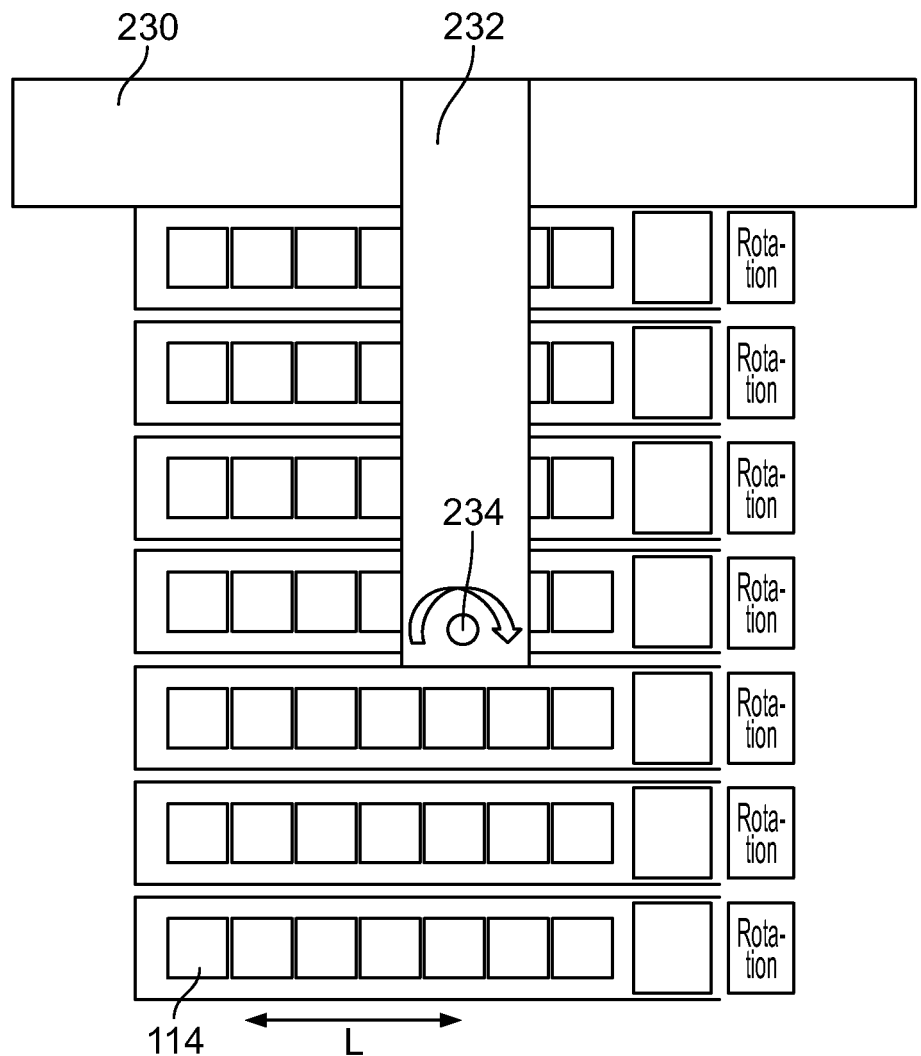
FIG. 8 is a diagram of another detector configuration in accordance with an embodiment.

For a 2D mode of operation, wherein the detector units 114 do oscillate, pivot, swivel, or rotate, the detector units 114 are positioned differently with respect to the examination axis. In particular, as shown in FIG. 8, the columns or rows of detector units 114 are rotated, in this embodiment 90 degrees, to extend perpendicular to the examination axis. This configuration allows for imaging as described in more detail herein. For example, the columns or rows of detector units 114 may rotate about a pivot 234 of the arm 232. Once rotated, the detector units 114 remain static within the row or columns (e.g., fixed relative orientation with respect to each other), but together may be shifted or moved as described herein.

Other variations are contemplated. For example, as shown in FIG. 9, an imaging system 240 includes a row of elongated detector units 242. For example, as compared to the detector units 114, the detector units 242 may be two to three time longer. However, other lengths may be provided as desired or needed. Accordingly, compared to the detector units 114, the detector units 242 extend along a greater length of the examination axis. In some embodiments, the detector units 242 may have the extended length along an axis transverse to the examination axis as shown in FIG. 10. As can be seen, each detector unit 114 provides coverage of the entire width of the subject 110 and/or patient table 120. In operation, with the configuration of FIG. 9, motion similar to FIG. 3 may be provided, and with the configuration of FIG. 10, motion similar to FIG. 6 may be provided. However, in these embodiments, the movement of the subject 110 is less as should be appreciated as a result of the lengthened detector units 242. For example, as shown in FIG. 11, complete coverage is provide with fewer incremental movements shown by the arrows 244 (or shorter overall travel distance).

Figure 15:
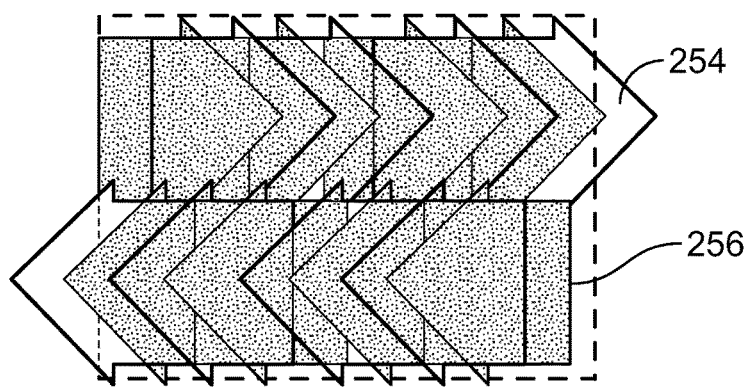
FIG. 15 is a diagram illustrating data acquisition scan movement in accordance with another embodiment.

As another example, as shown in FIG. 12, an imaging system 250 with detector units 252 aligned in a row similar to FIG. 2 are provided. However, in this embodiment, the detector units 252 may be elongated. As can be seen in FIG. 13, the detector units 252 may be rotated 90 degrees and the subject 110 moved along the examination axis. Thereafter, the entire row of detector units 252 may be shifted laterally and transverse to the examination axis as shown in FIG. 14 and the subject moved back in the opposite direction. Accordingly, each pass acquires data from about half or more of the subject 110 (e.g., left half and then right half as illustrated). It should be noted that some overlap may exist. Thus, as shown by the arrows 254 and 256 in FIG. 15, a two pass scan provides complete coverage wherein different sides of the subject 110 are scanned during each pass.

Figure 16:
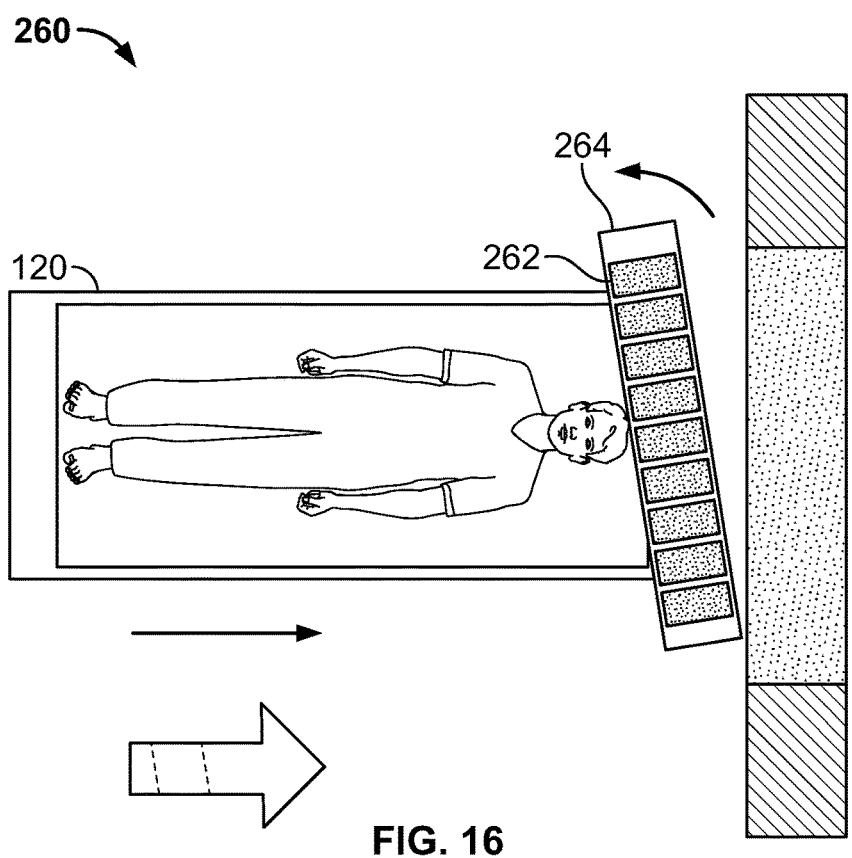
FIG. 16 is a diagram of an imaging system having a detector configuration in accordance with another embodiment.
Figure 17:
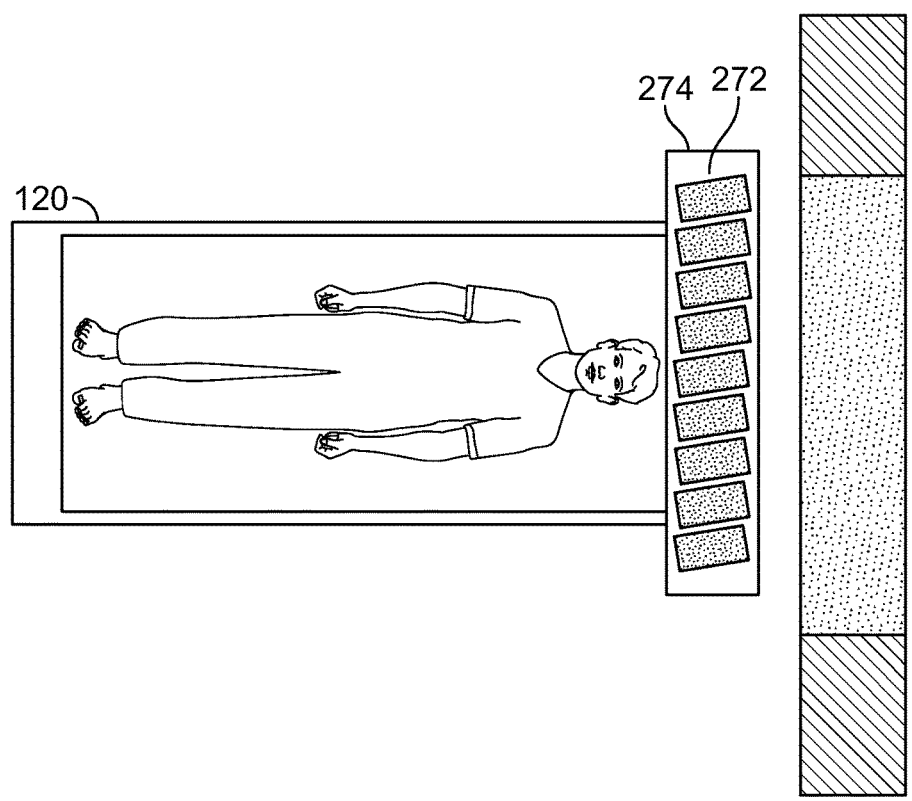
FIG. 17 is a diagram of an imaging system having a detector configuration in accordance with another embodiment.

As other examples, as shown in FIG. 16, an imaging system 260 may include a plurality of detector units 262 that form an array. However, in this embodiment, the support 264 holding the detector units 262 is moved or titled in a plane parallel to the patient table 120. For example, the detector units 262 are now at an angle relative to the examination axis. As should be appreciated this causes the gaps between the detector units 262 to overlap and provides more coverage. In the imaging system 270 shown in FIG. 17, a plurality of detector units 272 are provided that form an array supported by a support 274 holding the detector units 262. However, in this embodiment, the detector units 272 are moved or tilted in a plane parallel to the patient table 120. For example, the detector units 262 are again now at an angle relative to the examination axis, but the support 274 is not at an angle (e.g., detector units 262 titled within the support 274). As should be appreciated this causes the gaps between the detector units 272 to overlap and provides more coverage.

Figure 18:
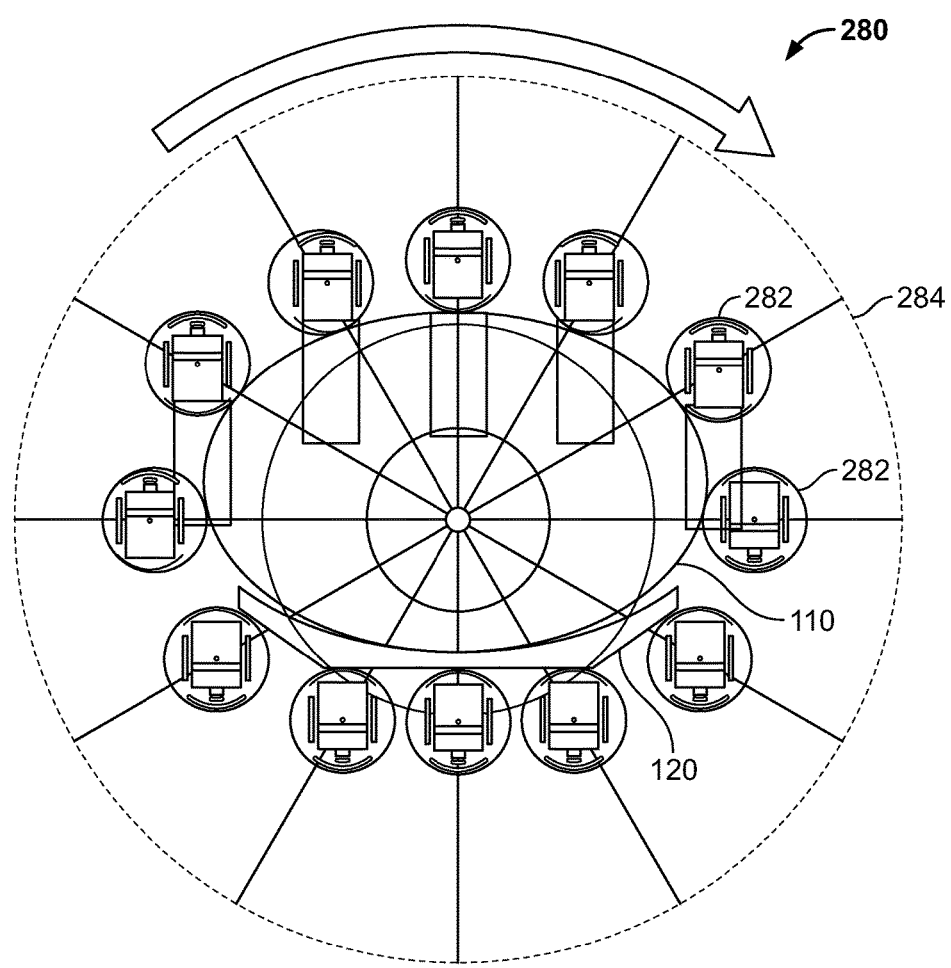
FIGS. 18-20 are diagrams illustrating data acquisition scan movement in accordance with another embodiment.
Figure 19:
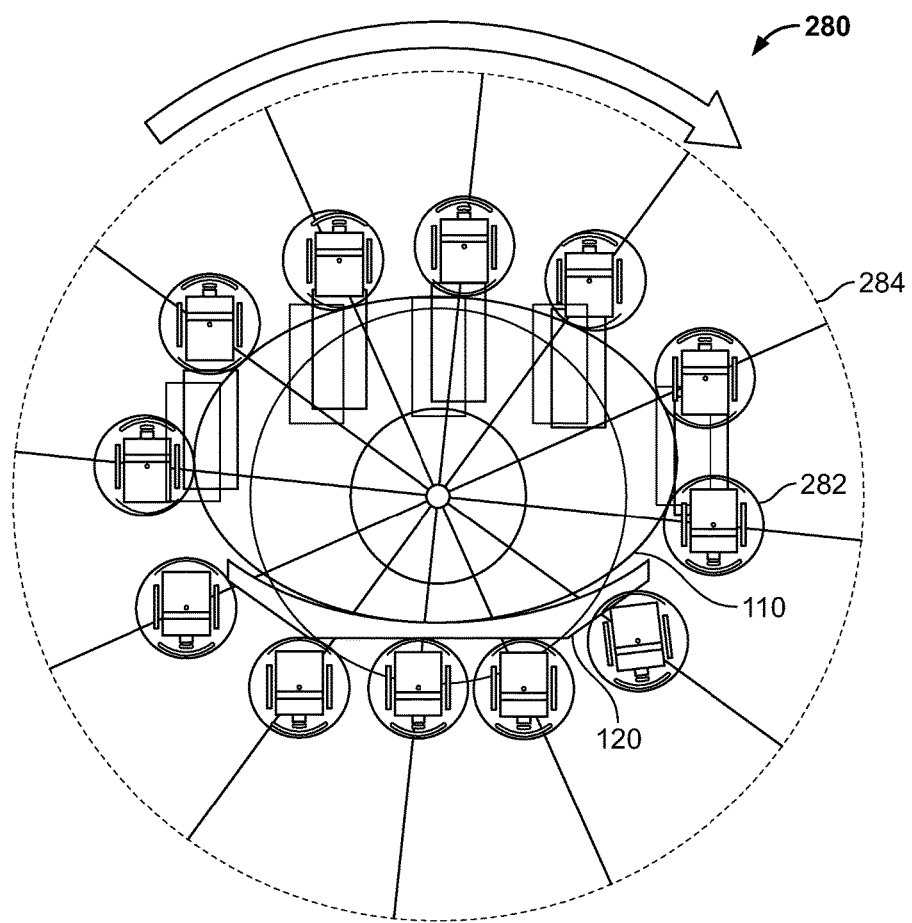
Figure 20:
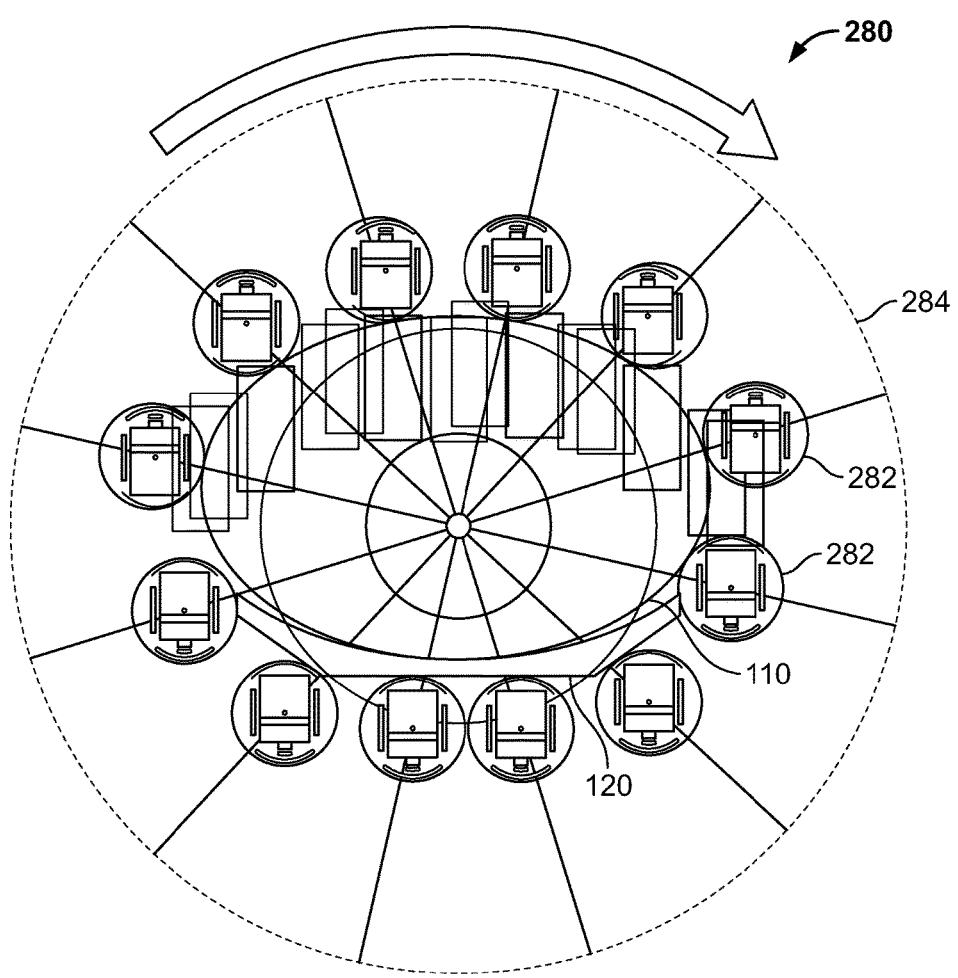

As another example, a system 280 may be provided as shown in FIG. 18 wherein the gantry 284 rotates while the detector units 282 (illustrated as detector heads) are vertical (relative to the patient table 120). This configuration may be referred to as an Iris configuration and in some embodiments the gantry 284 rotates until all of the gaps between the detector units 282 are covered. Then the detector units 282 are translated (e.g., in a stepwise operation) as shown in FIG. 19. As can be seen, some overlap in coverage is provided with the end detector units 282. The system 280 then advances the patient bed 120 as illustrated in FIG. 20.

Figure 21:
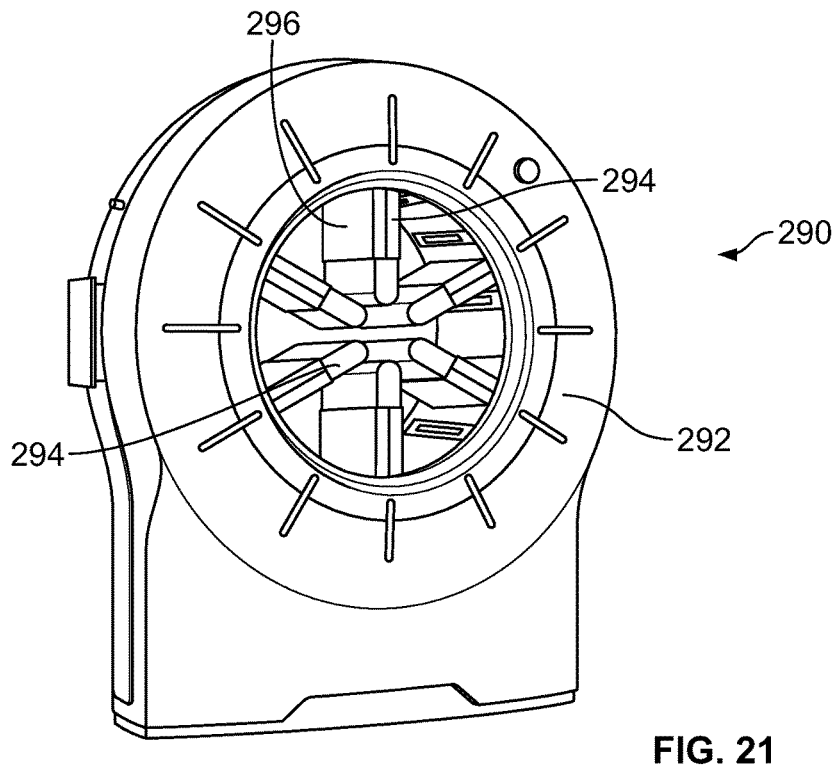
FIG. 21 is a perspective view of an imaging system in accordance with another embodiment.
Figure 22:
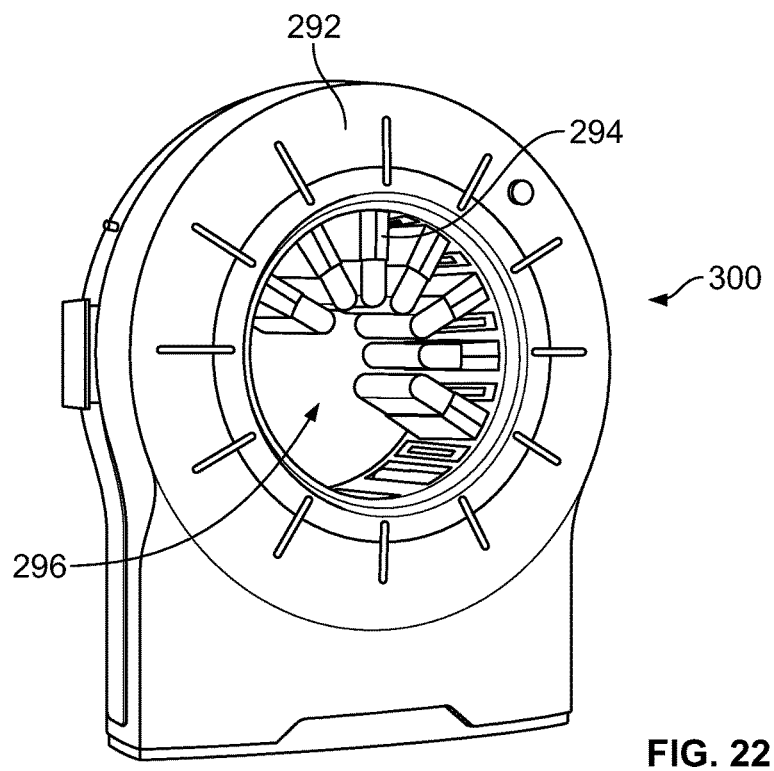
FIG. 22 is a perspective view of an imaging system in accordance with another embodiment.

It should be noted that a plurality of arms supporting the detector units may be provided in different configurations. For example, as shown in FIG. 21, a system 290 may be provided with a gantry 292 having a plurality of arms 294 (e.g., movable supports as described herein) that extend and/or are movable radially inward and outward from the gantry 292. It should be noted that the arms 294 are spaced apart circumferentially around the entire bore 296 in this embodiment. It also should be noted that additional or fewer arms and different spacing between arms 294 may be provided. The arms 294 may be movable as described herein and may be embodied as the detector carriers 116 (shown in FIG. 1) in some embodiments. Additionally, each arm 294 may support one or more detector units or modules (e.g., the detector units 114 shown in FIG. 1). Other variations include arms 294 that are provided along only a portion of the circumference of the bore 296 as illustrated in the system 300 of FIG. 22. It should be noted that although the arms 294 are illustrated along about 180 degrees, the arms 294 may be provided along more or less of the bore 296, such as more or less than 180 degrees.

Figure 23:
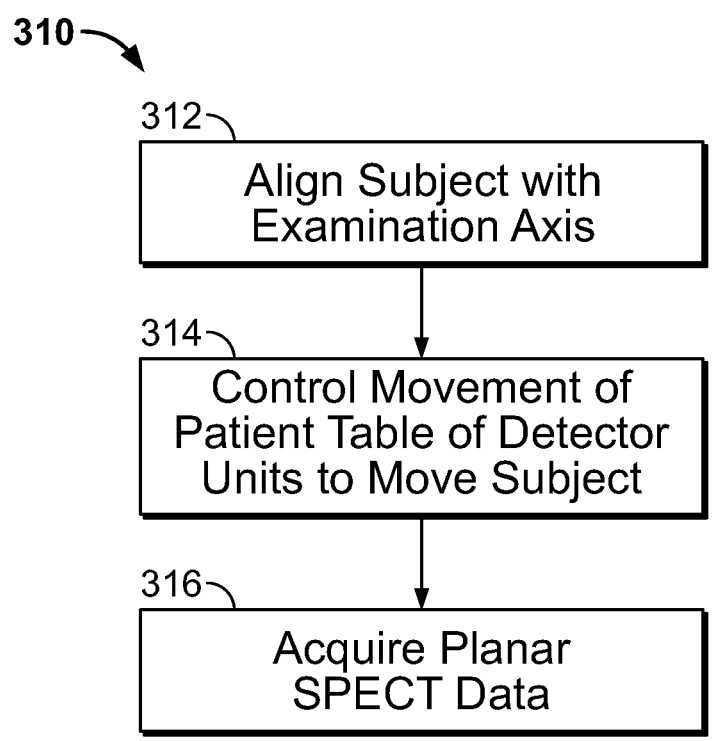
FIG. 23 is a flowchart of a method in accordance with various embodiments.

Thus, various embodiments provide planar SPECT imaging using different configurations and movements of detector units. In some embodiments, a method 310 as shown in FIG. 23 may be provided to perform 2D SPECT imaging. The method 310 includes aligning a subject with an examination axis at 312, for example, from head to toe on a patient table as described herein. The method 310 also includes controlling movement of the patient table or detector units at 314 to move the subject. For example, shifting movement of the detector units in combination with movement of the patient table may provide full scan coverage. However, while the detector units may form part of a SPECT camera that is operable based on swinging, pivoting or rotating heads or detector units, in various embodiments, the individual detector units are not moved, but instead may be moved together as a group as described herein to acquired 2D SPECT data.

The method 310 includes acquiring planar SPECT data at 316 as described herein.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An imaging system comprising:
a gantry having an opening therethrough;
a patient table movable through the opening of the gantry along an examination axis;
a plurality of detector units mounted to the gantry, the plurality of detector units movable to acquire Single Photon Emission Computed Tomography (SPECT) data, the plurality of detector units disposed in a series, with the series extending across a width of the patient table; and
a controller configured to control movement of the patient table and the plurality of detector units (i) as a group to acquire two-dimensional (2D) SPECT data, the plurality of detector units having detector faces oriented parallel to each other and in a common direction while moving together to acquire the 2D SPECT data, wherein the detector faces comprise corresponding detecting surfaces configured to receive radiation from an object being imaged, the detector surfaces parallel to the patient table when the detector faces are oriented parallel to each other and in the common direction, and (ii) individually to acquire three-dimensional (3D) SPECT data, the plurality of detector units individually moving with respect to each other when acquiring the 3D SPECT data, wherein the controller is configured to, in a series of alternating steps during imaging, shift the plurality of detector units in a first direction and subsequently move the patient table in a second direction perpendicular to the first direction to define a zig-zag scan pattern to acquire the 2D SPECT data.

2. The imaging system of claim 1, wherein the first direction is transverse to the examination axis.

3. The imaging system of claim 2, wherein the controller is configured to move the patient table along the examination axis in a direction opposite to the first direction after the detector units are shifted.

4. The imaging system of claim 1, further comprising an x-ray computed tomography (CT) imaging gantry positioned adjacent the gantry with the plurality of detector units.

5. The imaging system of claim 1, wherein the plurality of detector units are aligned in a plurality of rows, the controller further configured to rotate the plurality of rows relative to the examination axis to position the plurality of rows one of parallel or perpendicular to the examination axis.

6. The imaging system of claim 1, wherein the plurality of detector units are each sized to have a length that is equal to at least a width of the patient table.

7. The imaging system of claim 1, wherein the controller is further configured to rotate the plurality of detector units relative to the examination axis to position the plurality of detector units parallel to the examination axis and shift the plurality of detector units in a direction transverse to the examination axis, the controller also configured to move the patient table along the examination axis in one direction and in a different opposite direction after the detector units are shifted to acquire the 2D SPECT data.

8. The imaging system of claim 1, wherein the plurality of detector units are aligned in a plurality of rows such that the detector units in adjacent rows are offset relative to the examination axis.

9. A method to acquire two-dimensional (2D) Single Photon Emission Computed Tomography (SPECT) data, the method comprising:
aligning a patient table with an opening of a gantry and along an examination axis, the patient table movable through the opening of the gantry along the examination axis, a plurality of detector units mounted to the gantry, the plurality of detector units spaced apart from each other forming gaps between adjacent detector units, the plurality of detector units disposed in a series, with the series extending across a width of the patient table, the plurality of detector units configured to acquire Single Photon Emission Computed Tomography (SPECT) data; and
controlling movement of the patient table and the plurality of detector units to acquire two-dimensional (2D) SPECT data, the plurality of detector units remaining oriented parallel to each other and in a common direction while moving together to acquire the 2D SPECT data, wherein the detector units comprise corresponding detecting surfaces configured to receive radiation from an object being imaged, the detector surfaces parallel to the patient table when the detector units are oriented parallel to each other and in the common direction, wherein controlling the movement of the patient table and the plurality of detector units, in a series of alternating steps during imaging, shifting the plurality of detector units in a first direction and subsequently moving the patient table in a second direction perpendicular to the first direction to define a zig-zag scan pattern to acquire the 2D SPECT data.

10. The imaging system of claim 1, wherein at least one of the detector units is configured to acquire computed tomography (CT) data.

11. The imaging system of claim 1, wherein the plurality of detector units include corresponding detector heads mounted to the gantry via corresponding arms, wherein the controller is configured to pivot the detector heads while rotating the gantry to move the plurality of detector units while maintaining the detector units oriented parallel to each other and in a common direction.

* * * * *